US007541021B2

(12) United States Patent
Sambuco et al.

(10) Patent No.: US 7,541,021 B2
(45) Date of Patent: Jun. 2, 2009

(54) PROCESS FOR PREPARATION OF A STERILE SUSPENSION OF CORTICOSTEROID PARTICLES FOR THE ADMINISTRATION BY INHALATION

(75) Inventors: Barbara Sambuco, Parma (IT); Daniele Pirotta, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 208 days.

(21) Appl. No.: 10/510,232

(22) PCT Filed: Apr. 15, 2003

(86) PCT No.: PCT/EP03/03916

§ 371 (c)(1), (2), (4) Date: Apr. 11, 2005

(87) PCT Pub. No.: WO03/086347

PCT Pub. Date: Oct. 23, 2003

(65) Prior Publication Data

US 2005/0175546 A1 Aug. 11, 2005

(30) Foreign Application Priority Data

Apr. 17, 2002 (IT) ........................ MI2002A00808

(51) Int. Cl.
*A61K 9/12* (2006.01)

(52) U.S. Cl. ........................................................ 424/45
(58) Field of Classification Search .................... 424/45
See application file for complete search history.

(56) References Cited

U.S. PATENT DOCUMENTS 6,464,958 B1 * 10/2002 Bernini et al. ................ 424/43
2007/0140980 A1 * 6/2007 Capocchi et al. .............. 424/46

FOREIGN PATENT DOCUMENTS

WO 00 25746 5/2000

OTHER PUBLICATIONS

Applicants' response to Examiner in corresponding application filed in European Patent Office dated Jul. 18, 2005.

* cited by examiner

*Primary Examiner*—Mina Haghighatian
(74) *Attorney, Agent, or Firm*—Oblon, Spivak, McClelland, Maier & Neustadt, P.C.

(57) ABSTRACT

A process for the preparation of aqueous suspensions of sterile micronized drug particles, in particular corticosteroid, to be administered by inhalation, which produces homogenous dispersions of particles characterized by optimal size and size distribution is disclosed. The process is carried out by using a turboemulsifier equipped with a high-power turbine and connected to a loading hopper.

14 Claims, 2 Drawing Sheets

Figure 2 – Particle distribution frequency according to size ranges, expressed by the Feret diameter determined microscopically: a) obtained by the process according to the invention; b) obtained by the process described in WO 00/25746.
Relative frequency %
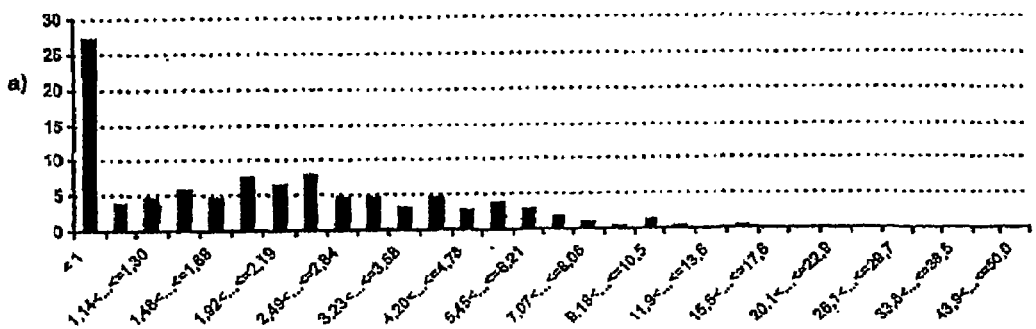
Feret Diameter (μm)
Relative frequency %
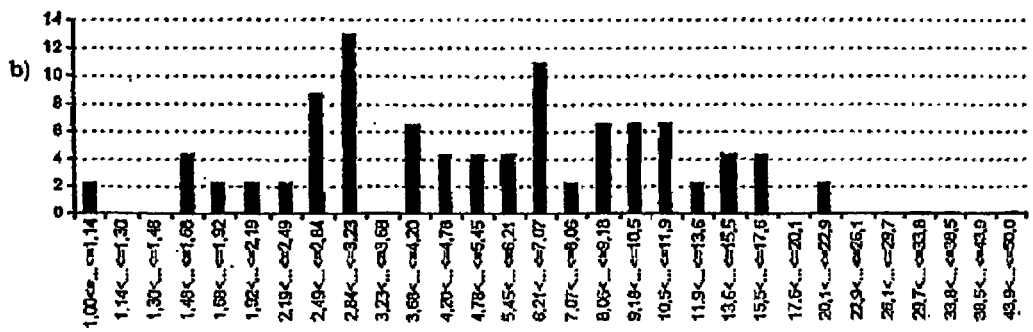
Feret Diameter (μm)

PROCESS FOR PREPARATION OF A STERILE SUSPENSION OF CORTICOSTEROID PARTICLES FOR THE ADMINISTRATION BY INHALATION

The present invention relates to a process for the preparation of aqueous suspensions of drug particles, to be administered by inhalation, which produces homogenous dispersions of particles characterised by optimal size and size distribution.

PRIOR ART

The method of delivering drugs by inhalation has been used for several years, and is the mainstay of the treatment of diseases that limit the respiratory flow, such as asthma and chronic bronchitis.

The advantages of inhalation over the systemic route include the fact that the drug is released directly at the site of action, thus preventing systemic side effects and resulting in a more rapid clinical response and a higher therapeutic index.

Among the various types of drug which are administered by inhalation for the treatment of the respiratory diseases, corticosteroids, such as beclomethasone dipropionate (BDP), mometasone furoate, flunisolide, budesonide, fluticasone propionate and others are of great importance. They are generally administered in micronised form in suspension, in an aqueous phase that usually also contains surfactants and/or cosolvents, or in a propellant. The drug is inhaled in aerosol form, ie. in the form of a dispersion of solid particles in a gaseous medium. The efficacy of this form of administration depends on the deposit of a sufficient quantity of particles at the site of action.

In order to ensure an effective penetration into the low respiratory tract of the patient, i.e. bronchioli and alveoli, one of the most important parameters is particle size, which must be equal or lower than 5-6 μm. This size is quantified by measuring a characteristic sphere-equivalent diameter, known as the median aerodynamic diameter (MAD), which expresses the ability of particles to be transported in suspension in an air flow.

Particles with a larger MAD are ineffective because they are deposited in the oropharyngeal cavity, and are therefore unable to reach the terminal branches of the respiratory tree; they can also give rise to local side effects, or may be absorbed through the buccal mucosa and give rise to systemic side effects.

Another important characteristic to ensure correct administration, and therefore therapeutic efficacy, is homogenous dispersion of the particles in suspension, without the formation of aggregates which prevent correct aerosolisation. The formation of more or less compact aggregates can also give rise to problems of distribution and therefore of uniformity of dose during the filling of the containers. From the technological standpoint it is also very important for the particles to fall within the narrowest and most homogenous possible size distribution range, and to be as finest as possible compatibly with the upper limit (5-6 μm); this because upon variation of environmental humidity conditions, aqueous phase suspensions may face problems over time in terms of constancy of particle distribution due to the total or partial recrystallisation of the small amount of dissolved solute (Davis S et al Int J Pharm 1, 303-314, 1978; Tiano S et al Pharm Dev Tech 1, 261-268, 1996; Taylor K et al Int J Pharm 153, 93-104, 1997). As this parameter is inversely correlated with the MAD of the particles, such an increase can prejudice the efficacy of nebulisation and therapeutic efficacy, as particles with an MAD exceeding 5-6 μm are unable to reach the preferential site of action.

Therefore the finer the particles, the lower the probability that after partial recrystallisation they will reach the critical size liable to prejudice the properties of the formulation in terms of technological and therapeutic parameters.

Another important requirement that must be met by pharmaceutical formulations for inhalation is sterility. This requirement is becoming more and more mandatory as confirmed by the FDA final rule "*Sterility Requirement for Aqueous-Based Drug Products for Oral Inhalation*" published in the Federal Register of May 26, 2000 (65 FR 34082) governing the quality and safety of pharmaceutical products for a number of reasons, including the fact that the lungs are a particularly vulnerable organ of the human body, and many patients who use inhaled drugs have general health problems.

The current trend is to produce inhalation formulations devoid of preservatives and bacteriostatics, as it has been reported in the literature that some of the substances commonly used for this purpose can induce allergic reactions or give rise to irritation of the respiratory mucosae (Menendez R et al J *Allergy Clin Immunol* 84, 272-274, 1989; Afferty P et al *Thorax* 43, 446-450, 1988). Various processes can be used to manufacture sterile pharmaceutical formulations for inhalation. For example, the active ingredient can be sterilised by dry heating or irradiation, followed by preparation of the formulation under aseptic conditions, or the formulation can be pre-prepared and sterilised by treatment in an autoclave or by filtration.

Some of the sterilisation methods reported suffer from drawbacks or limitations. For example, heat treatments are unsuitable in the case of aqueous suspensions of thermolabile corticosteroids such as beclomethasone dipropionate (BDP), and sterilising filtration is not feasible for suspensions.

WO 99/25359 relates to a process for sterilising corticosteroids by heating them at lower temperatures than those reported in some Pharmacopoeias (110-130° C. vs 140-180° C.) but does not contain any teaching as to how to prepare the relevant pharmaceutical formulations in the form of suspensions.

In the patent application WO 00/25746, the applicant described a process for the preparation of aqueous suspensions for nebulisation based on a micronised active ingredient sterilised with gamma rays.

Said process basically involves a first stage of preparation of an aqueous solution, which constitutes the vehicle and contains suitable excipients, in a turboemulsifier, followed by the addition of a sterile micronised active ingredient which in turn is dispersed at atmospheric pressure in the same turboemulsifier. The dispersion of the active ingredient in the aqueous phase may be subjected to an additional high-pressure homogenising treatment which further reduces the average size of the particles in suspension.

In the text an example (Ex. 2) of preparation of a suspension formulation on a pilot scale (100 litres) starting from micronised BDP sterilised by gamma radiation is reported. In said example, the active ingredient is added to the sterile aqueous base and dispersed, initially using magnetic agitation only, then by using a turbine system for 15-20 minutes.

However, when this process has been applied on an industrial scale, it has been found that long processing times are required for the homogenisation stage. A mixing time of over two hours is required for preparations exceeding 1000 litres. Moreover, the obtained dispersions do not meet the requirement of homogeneity in a satisfactory way.

It has been observed that these drawbacks are largely attributable to the technological characteristics of the sterile micronised active ingredient, which disperses more slowly as well as more difficulty in the aqueous vehicle than the unsterilised compound. In fact, sterile micronised corticosteroid particles must be stored under vacuum to maintain their sterility, and consequently tend to pack more strongly than non-sterile particles of the same active ingredient, as demonstrated by density measurements. Stronger packing is in turn responsible for difficulties with dispersion.

SUMMARY OF THE INVENTION

A process for the preparation on an industrial scale of aqueous suspensions for nebulisation comprising a sterile micronised active ingredient, preferably sterilised by irradiation with gamma rays has now been found, and its the object of this invention. The process according to the invention reduces processing times and gives rise to suspensions with a homogenous, reproducible particle distribution and optimum particle-size distribution, thus producing compositions with a high level of physical stability and therapeutic efficacy. Suspensions obtained with the process according to the invention are used as pharmaceutical formulations for aerosol inhalation after being introduced into suitable containers such as multidose vials for nebulisation, and preferably monodose vials.

In the embodiment of the invention, the process is carried out with the use of a turboemulsifier fitted with a high-power turbine, and is characterised in that the active ingredient in powder form is transferred through the turbine by exploiting the vacuum applied in the turboemulsifier. On the contrary, in the prior art, the active ingredient is added from the top directly into the turboemulsifier.

It has now been found that by operating in accordance with the teaching of this invention, i.e. by loading the sterile active ingredient into the turboemulsifier through the turbine after applying the vacuum rather than loading it from the top at atmospheric pressure, far more efficient dispersal of the active ingredient, and therefore homogenous suspensions with a distribution reproducible from one batch to another, can be obtained in a much shorter time, on an industrial scale. By operating under vacuum it is also possible to prevent foam formation, and therefore the additional operation to remove it. Moreover, it has been unexpectedly found that finer particles with a narrower, more homogenous particle-size distribution range can be obtained by the process of the invention, with no need for further treatments such as treatment in a high-pressure homogeniser as described in WO 00/25746. As already mentioned, these properties give rise to significant advantages during the step of filling the bulk suspension into suitable containers (multidose or monodose vials) and during storage.

In suspensions obtained with the process according to the invention, the particles sediment more slowly because of their finer size, in accordance with Stokes' law, expressed by the formula:

$$V = \frac{d^2(\rho - \rho_0)g}{18\eta}$$

wherein V is the sedimentation rate, d is the mean diameter of the particles, $\eta$ is the viscosity of the medium in poises, $\rho$ is the density of the particles, $\rho_0$ is the density of the dispersing medium, and g is the gravity acceleration.

During the container-filling step, the re-circulation conditions to which the particles of active ingredient are subjected are sufficient to achieve uniform distribution of the particles in the containers, as they pass through the system of radial nozzles of the turbine, and there is no need to use external elements such as pipes or blades to maintain the particles in suspension. The use of such elements would make it necessary to open the apparatus periodically for cleaning operations, thus prejudicing continuity of manufacture under sterile conditions. In the process of the invention, the particles not only sediment more slowly, but also are less liable to form agglomerates, which means that once introduced into the vials, the suspensions will be more physically stable, and the storage period can be increased. The formation of agglomerates, especially "cakes", ie. sets of highly compact suspended particles, can prejudice the correct dosage of the drug, or at least make administration less therapeutically effective, as the dose may be transferred incompletely from the vial to the bulb of the nebuliser apparatus.

BRIEF DESCRIPTION OF THE DRAWINGS

FIG. 2 shows the particle distribution frequency according to size ranges, expressed by the Feret diameter determined microscopically: a) obtained by the process according to the invention; b) obtained by the process described in WO 00/25746.

DETAILED DESCRIPTION OF THE INVENTION

Figure 1:
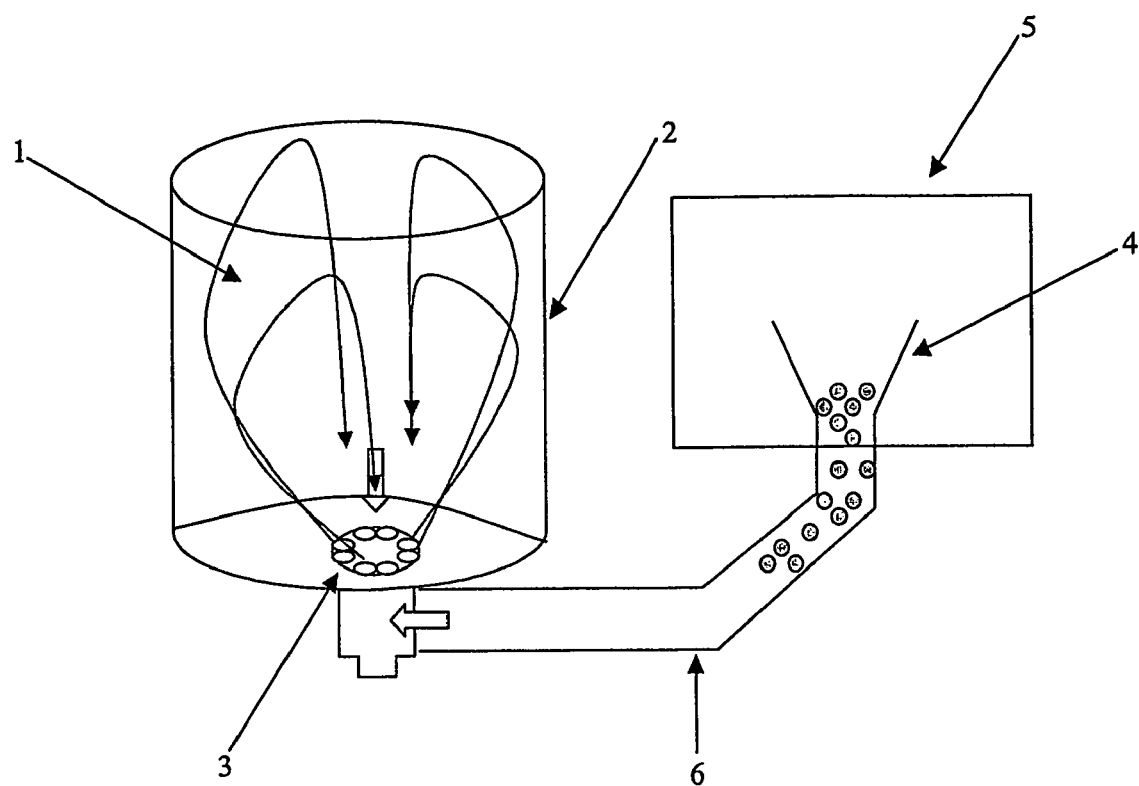
FIG. 1 schematically shows the apparatus of the invention of a turboemulsifier combined with a feed hopper.

The invention will now be described in detail by reference to FIG. 1, which shows a scheme of a plant that can be used for the process according to the invention.

A vacuum turboemulsifier (1), constituted by a steel container (2) and fitted with a high-power turbine, and possibly with an agitation system, can be advantageously used to prepare the suspension. "High-power turbine" means a turbine with a power of between 15 to 55 Kwatts. A turboemulsifier, which can agitate the suspension via the system of radial nozzles of the turbine (3), through which the active ingredient passes, will preferably be used, fitted with a 30 Kwatt turbine.

The system is also equipped with a hopper (4) fitted inside an isolator (5) and connected to the turbine of the turboemulsifier via a rigid pipe or hose (6) for the purpose of loading the powder. The entry of the powder into the pipe can be regulated by a butterfly valve to minimise the quantity of incoming air which can contribute to foam formation. "Isolator" means a transparent container, generally made of plexiglas or polyvinylchloride (PVC), fitted with one or more entrance doors and handling gloves for transfer of the powder.

The first stage of the preparation process involves preparing the aqueous solution constituting the vehicle in a suitable tank, preferably made of stainless steel; the solution, which can be sterilised by heat or filtration, may contain suitable additives or excipients, preferably selected from wetting agents such as polysorbate 20 or sorbitan monolaurate, isotonic agents such as sodium chloride, and optionally stabilising agents such as disodium edetate and/or buffers. The vehicle is preferably sterilised at 121° C. for 20 minutes. If necessary, the solution thus obtained is subjected to clarifying filtration and transferred to a turboemulsifier equipped with a vacuum pump. At the second stage, after applying the vacuum in the turboemulsifier, one or more sterile micronised active ingredients are added to the aqueous medium by introducing them from the loading hopper through the turbine.

Alternatively, the aqueous solution constituting the vehicle can be prepared and sterilisation performed in a turboemulsifier fitted with a jacket suitable both for steam heating and water cooling.

Advantageously, the active ingredient will be a corticosteroid such as beclomethasone dipropionate, mometasone furoate, fluticasone propionate, flunisolide, ciclesonide or budesonide, micronised by usual processes and sterilised by radiation or heating. Preferably, the active ingredient will be micronised beclomethasone dipropionate sterilised by treatment with gamma rays under the conditions reported in WO 00/25746. At the third stage, the active ingredient is homogenised, again under vacuum, using the turbine system and operating at a speed of between 750 and 4000 rpm, preferably between 1000 and 3600 rpm, and even more preferably between 1600 and 3000 rpm, for 5-60 minutes, and preferably for 20-40 minutes. In the preferred conditions a turbine system operating at 2900 rpm for 30 minutes is used.

The suspension of micronised product obtained at the end of the treatment is distributed into suitable containers, preferably constituted by pre-formed monodose vials for nebulisation, optionally pre-sterilised by beta rays irradiation or made with the "blow, fill and seal" technology.

As a consequence, this invention also relates to pharmaceutical formulations to be used for nebulisation, preferably in unit dose preparations containing the aqueous suspensions obtained by the process according to the invention.

In said formulations, the Feret diameter of at least 90% of the suspended particles in the final container will advantageously be less than or equal to 8 μm. Preferably, the diameter of at least 50% of the particles will be less than 3 μm, and that of at least 90% less than 7 μm. Even more preferably the diameter of at least 50% of the particles will be less than 2.5 μm, and that of at least 90% less than 6 μm. "Feret diameter" means the distance between imaginary parallel lines tangential to a randomly oriented particle and perpendicular to the ocular scale (USP 26, 2003, page 2185).

The dimensional characteristics of the particles were also evaluated by using a Malvern apparatus. This type of test exploits the diffraction of a laser beam by the particles to determine the size distribution of the particles in suspension. The parameter considered is the median volumetric diameter in μm of 10%, 50% and 90% of the particles, expressed as d(v,0.1), d(v,0.5) and d(v,0.9) respectively, which is determined by assuming that the particles have a geometrical shape equivalent to a sphere. Advantageously, in the suspension formulation of the invention, the d(v,0.9) after sonication is less than 8 μm and the d(v,0.5) is comprised between 2 and 3.5 μm. More preferably the d(v,0.9) is less than 7 μm, the d(v,0.5) is between 2.5 and 3 μm and the particle size distribution (i.e. the difference between d(v,0.9) and d(v, 0.1) does not span for more than 7 μm, preferably for more than 6 μm.

The concentration of active ingredient in the pharmaceutical formulations according to the invention is between 0.01 and 0.1% w/v, preferably 0.04% w/v in the case of BDP and 0.025-0.05% in the case of budesonide.

A further object of this invention is the use of the pharmaceutical formulations in unit dose preparations containing the aqueous suspensions obtained by the process according to the invention to treat lung diseases such as asthma and chronic bronchitis with a single daily administration.

As reported in the literature for budesonide (Tunek et al. Drug Metab Dispos 1997, 25, 1311-1317), it has been found that stable esters of the active metabolite of BDP, namely beclomethasone-17-monopropionate (17-BMP), are formed in the microsomes of human lung cells with long-chain fatty acids such as oleic acid.

These esters are retained in the cells much longer than the parent steroid and release the unchanged active ingredient in a controlled manner, so that the period of tissue exposure to the drug is increased.

It has also been observed that due to the formation of the monoester in the lung cells, the elimination half-life and the mean residence time of 17-BMP are longer after the administration of aqueous suspensions of BDP by nebulisation than formulations in suspension administered in the form of pressurised aerosols.

This last finding has been attributed to the particle distribution obtained after (re)suspension of the micronised active ingredient in the aqueous vehicle. As it can be appreciated from Table 2 and FIG. 2 of Example 3 the particles of the sterile micronised active ingredient of the aqueous suspension according to the invention are indeed much finer than those obtained according to the prior art and have a narrower and more homogeneous particle size distribution too. Said particles can more easily dissolve in the lung fluids and penetrate into the cells in a better way, enabling the active ingredient, due to the formation of the esters into the cells, to persist at the site of action for a longer period, so giving rise to a prolonged activity.

As a consequence of the optimal characteristics in term of particle size of the suspension formulations achieved by the process according to the invention, as well as of the behaviour observed for their active metabolites, pharmaceutical formulations for nebulisation of BDP and budesonide useful for treating lung diseases with a single daily administration can be obtained.

This constitutes a considerable advantage in terms of compliance by patients.

The invention is more particularly illustrated in the examples below.

EXAMPLES

Example 1

Technological Characteristics of Micronised Beclomethasone Dipropionate (BDP) Sterilised by Irradiation with Gamma Rays Compared with the Equivalent Unsterilised Product Sterile micronised BDP was obtained as described in WO 00/25746.

The apparent volumes and densities were measured according to the European Pharmacopoeia, 4th edition, paragraph 2.9.15.

100 g of the test substance is introduced into a dry 250 ml cylinder without compacting it. The unsettled apparent volume (Vo) is read off, then 10, 500 and 1250 taps are performed, and volumes ($V_{10}$, $V_{500}$ and $V_{1250}$) are read. If the difference between $V_{500}$ and $V_{1250}$ is greater than 2 ml, 1250 further taps are performed ($V_{2500}$).

Table 1 shows: i) the apparent density before settling (dv), which is the ratio between weight (g) and volume before settling (ml); ii) the apparent density after packing (ds), which is the ratio between weight (g) and the volume after compacting (ml); iii) packing capacity (Cs), which is the difference between $V_{10}$ and $V_{500}$ (ml).

The dimensional characteristics of the particles were evaluated by a Malvern apparatus. The results are set out in Table 1.

TABLE 1

Technological characteristics of micronised BDP before and after sterilising radiation

|  | Non-irradiated BDP | Irradiated BDP |
|---|---|---|
| Technological characteristics |  |  |
| dv (g/ml) | 0.21 | 0.32 |
| ds (g/ml) | 0.27 | 0.42 |
| Cs (ml) | 16 | 12 |
| Particle size (μm, Malvern) |  |  |
| d (v, 0.1) | 0.49 | 0.48 |
| d (v, 0.5) | 1.91 | 1.81 |
| d (v, 0.9) | 5.98 | 5.73 |

The results demonstrate that after radiation, although BDP does not undergo any variations in particle size, it is packed to a greater extent than the non-irradiated product, as indicated by the "packing capacity" value (Cs).

Example 2

Preparation of a Sterile Suspension of Micronised BDP Sterilised with Gamma Rays Composition:

| Ingredients | Total amount of the preparation | Amount per pharmaceutical unit |
|---|---|---|
| Sterile micronised BDP | 0.6 kg | (0.8 mg) |
| Polysorbate (Tween) 20 | 1.5 kg | (2.0 mg) |
| Sorbitan monolaurate | 0.3 kg | (0.4 mg) |
| Sodium chloride | 13.5 kg | (18.0 mg) |
| Water for injection q.s. for | 1500 l | (2.0 ml) |

The first stage of preparation of the sterile suspension involves preparing the aqueous base in a Unimix turboemulsifier fitted with a 30 Kwatt turbine.

After loading water for injection at 60-70° C. into the apparatus, sodium chloride and surfactants are added, and the preparation is mixed with the turbine to obtain a homogenous dispersion of the surfactants.

The preparation is then sterilised in a turboemulsifier fitted with a jacket suitable for both steam heating and water cooling; the sterilisation treatment is conducted at 121° C. for approx. 20 minutes.

After filtering and cooling the preparation to the temperature of 30-35° C., a vacuum is applied in the turboemulsifier and the sterile BDP is transferred to the sterile aqueous vehicle through the turbine using the vacuum applied. The active ingredient is dispersed under vacuum along the whole homogenisation stage using the turbine system at 2900 rpm for 30 minutes.

The turboemulsifier is subsequently connected via sterile piping to the storage tank of the container-filling machine and positioned under laminar-flow hood in a controlled-contamination environment, and the suspension is distributed in monodose vials to the volume of 2.15 ml using the "blow, fill and seal" technology.

Example 3

Particle-Size Analysis of Preparations Obtained According to Example 2

The dimensional characteristics of the particles were evaluated by using a Malvern apparatus and by microscopy.

The Malvern tests were conducted as reported in Example 1. The median volumetric diameter of the particles was determined before and after sonication.

For the purpose of examination under the microscope, a drop of suspension was placed on a slide and covered with a slide cover. The diameter of the particles, expressed as the Feret diameter, was measured with the aid of a micrometer.

The results, expressed as d(v,0.1), d(v,0.5) and d(v,0.9), i.e. as the diameter in μm of 10%, 50% and 90% of the particles, are set out in Table 2, for the purpose of comparison with those relating to a suspension obtained as described in WO 00/25746.

The data relating to the relative distribution frequency of the particle diameters, measured microscopically, are shown in FIG. 2, for suspensions obtained with the process according to the invention (a) and according to the process described in WO 00/25746 (b) respectively.

TABLE 2

Particle-size characteristics of two sterile suspensions of BDP prepared according to example 2 (Prep. 1) and according to the process described in WO 00/25746 (Prep. 2) respectively.

| Particle-size characteristics | Prep. 1 (μm) | Prep. 2 (μm) |
|---|---|---|
| Feret Diameter (microscopy) |  |  |
| d(0.1) | 0.35 | 2.04 |
| d(0.5) | 1.82 | 5.75 |
| d(0.9) | 5.18 | 13.89 |
| Median volumetric diameter (Malvern) without sonication |  |  |
| d(v, 0.1) | 0.78 | 1.32 |
| d(v, 0.5) | 2.97 | 6.54 |
| d(v, 0.9) | 7.88 | 15.94 |
| Median volumetric diameter (Malvern) after sonication |  |  |
| d(v, 0.1) | 0.77 | 0.96 |
| d(v, 0.5) | 2.59 | 4.51 |
| d(v, 0.9) | 6.25 | 11.54 |

The results shown in Table 2 and FIG. 2 confirm that the process according to the invention produces finer particles with a narrower and more homogenous particle-size distribution.

The invention claimed is:

1. A process for the preparation on an industrial scale of an aqueous suspension comprising particles of an active ingredient for use as a pharmaceutical formulation for inhalation by nebulization, which comprises:

in a turboemulsifier apparatus comprised of a circular container having a base with an opening therein which receives a turbine device and which contains an aqueous solution, equipped with a vacuum pump, and a loading hopper, which contains a sterile micronized active ingredient, connected to said turbine by a conduit:

a) applying a vacuum to the turboemulsifier;

b) loading the sterile micronized active ingredient into the aqueous solution to form a dispersion of the micronized active ingredient; and c) stirring and homogenizing the micronized active ingredient in the aqueous suspension by operating the turbine, wherein the micronized active ingredient is loaded in the aqueous solution through the turbine, and whereby the median volumetric diameter of 90% of the suspended particles of the active ingredient is less than 8 micron and that of at least 50% ranges from 2 to 3.5 micron.

2. The process as claimed in claim 1, wherein the homogenized suspension is distributed into containers.

3. The process as claimed in claim 1, wherein the aqueous solution contains additives or excipients selected from the group consisting of wetting, stabilizing, isotonic and buffering agents.

4. The process as claimed in claim 1, wherein the micronized active ingredient is a corticosteroid.

5. The process as claimed in claim 1, wherein the aqueous solution has been sterilized by heat or filtration.

6. The process as claimed in claim 4, wherein the micronized corticosteroid is sterilized by irradiation or by heat.

7. The process as claimed in claim 4, wherein the micronized corticosteroid is beclomethasone dipropionate which is sterilized by being subjected to gamma radiation.

8. The process as claimed in claim 1, wherein the homogenization of the suspension is conducted at a turbine speed ranging from 750 to 4000 rpm for 5 to 60 minutes.

9. The process as claimed in claim 8, wherein the homogenization conditions are a turbine speed ranging from 1600 to 3000 rpm for 20 to 40 minutes.

10. The process as claimed in claim 9, wherein homogenization is achieved at a turbine speed of 2900 rpm for 30 minutes.

11. The process as claimed in claim 1, wherein said containers are monodose vials.

12. The process as claimed in claim 1, wherein the turbine is provided with a radial nozzle system.

13. The process as claimed in claim 3, wherein the isotonic agent is sodium chloride.

14. The process as claimed in claim 3, wherein the wetting agent is selected from the group consisting of polysorbate 20 and sorbitan monolaurate.

* * * * *